United States Patent
Ross et al.

(10) Patent No.: US 9,907,589 B2
(45) Date of Patent: Mar. 6, 2018

(54) SURGICAL PLATE DEVICE INCORPORATING A SCREW LOCKING MECHANISM

(71) Applicants: Thomas Ross, Austin, TX (US); Charles W. Mumme, Austin, TX (US); John C. Steinmann, Redlands, CA (US); John P. Steinmann, Redlands, CA (US); Trace R. Cawley, Boca Raton, FL (US)

(72) Inventors: Thomas Ross, Austin, TX (US); Charles W. Mumme, Austin, TX (US); John C. Steinmann, Redlands, CA (US); John P. Steinmann, Redlands, CA (US); Trace R. Cawley, Boca Raton, FL (US)

(73) Assignee: RENOVIS SURGICAL TECHNOLOGIES, INC., Redlands, CA (US)

( * ) Notice: Subject to any disclaimer, the term of this patent is extended or adjusted under 35 U.S.C. 154(b) by 9 days.

(21) Appl. No.: 14/828,934

(22) Filed: Aug. 18, 2015

(65) Prior Publication Data

US 2017/0049491 A1 Feb. 23, 2017

(51) Int. Cl.
*A61B 17/56* (2006.01)
*A61B 17/80* (2006.01)
*A61B 17/70* (2006.01)

(52) U.S. Cl.
CPC ...... *A61B 17/8042* (2013.01); *A61B 17/7059* (2013.01)

(58) Field of Classification Search
CPC .................................................. A61B 17/8042
USPC .................................................. 606/289–296
See application file for complete search history.

(56) References Cited

U.S. PATENT DOCUMENTS

| | | | | |
|---|---|---|---|---|
| 2004/0158246 | A1* | 8/2004 | Assaker | A61B 17/8042 606/296 |
| 2005/0261690 | A1* | 11/2005 | Binder | A61B 17/1728 606/295 |
| 2008/0287999 | A1* | 11/2008 | Markworth | A61B 17/7059 606/280 |
| 2011/0029023 | A1* | 2/2011 | Tornier | A61B 17/8042 606/289 |
| 2012/0158056 | A1* | 6/2012 | Blain | A61B 17/7059 606/246 |
| 2012/0232595 | A1* | 9/2012 | Holschlag | A61B 17/8042 606/280 |
| 2012/0289978 | A1* | 11/2012 | Jacob | A61B 17/8042 606/151 |

* cited by examiner

*Primary Examiner* — Jan Christopher Merene
(74) *Attorney, Agent, or Firm* — Clements Bernard Walker PLLC; Christopher L. Bernard

(57) ABSTRACT

A surgical plate device that incorporates a screw locking mechanism in each screw hole by which the surgical plate device is affixed to a bony segment. The screw locking mechanism includes a tab structure emanating from an interior portion (or either surface) of the surgical plate that is biased into a portion of the corresponding screw hole. When a screw is inserted into the screw hole, the head of the screw temporarily biases the tab structure out of the screw hole, until the head of the screw passes below the plane of the tab structure, at which point the tab structure rebounds into the previously occupied portion of the screw hole, thereby covering a portion of the head of the screw and preventing it from "backing out."

12 Claims, 6 Drawing Sheets

SURGICAL PLATE DEVICE INCORPORATING A SCREW LOCKING MECHANISM

FIELD OF THE INVENTION

The present invention relates generally to a surgical plate device incorporating a screw locking mechanism for stabilizing and securing adjacent bony segments in a surgical procedure. More specifically, the present invention relates to a cervical plate device incorporating a screw locking mechanism for stabilizing and securing adjacent vertebrae in a spinal surgical procedure.

BACKGROUND OF THE INVENTION

During a spinal surgical procedure, for example, a cervical plate or the like is used to aide in the fusion of adjacent vertebrae, providing required stability and security after a damaged intervertebral disc has been removed from and an intervertebral cage and/or bone graft have been placed into the intervertebral space of interest. This cervical plate or the like is typically secured to the adjacent vertebrae via a plurality of cervical plate screws, well known to those of ordinary skill in the art. One problem that is often encountered is that these cervical plate screws tend to "back out" over time, thereby allowing the cervical plate or the like to loosen and the entire construct to fail. Various cervical plate screw locking mechanisms have been designed and manufactured to alleviate this "backing out" problem, however, such conventional cervical plate screw locking mechanisms have typically been ineffective and/or overly complicated, sacrificing the desirable low profile nature of the cervical plate or the like, for example, and/or increasing its ease of use and cost. Further, many of these conventional cervical plate screw locking mechanisms undesirably contact the associated cervical plate screws when placed, resulting in potential wear and binding issues over time. Thus, an improved cervical plate or the like and cervical plate screw locking mechanism are still needed in the art.

BRIEF SUMMARY OF THE INVENTION

In various exemplary embodiments, the present invention provides a surgical plate device that incorporates a screw locking mechanism in each screw hole by which the surgical plate device is affixed to a bony segment. The screw locking mechanism includes a tab structure emanating from an interior portion (or either surface) of the surgical plate that is biased into a portion of the corresponding screw hole. When a screw is inserted into the screw hole, the head of the screw temporarily biases the tab structure out of the screw hole, until the head of the screw passes below the plane of the tab structure, at which point the tab structure rebounds into the previously occupied portion of the screw hole, thereby covering a portion of the head of the screw and preventing it from "backing out." To achieve this functionality, the tab structure translates along a slot and pin or other track structure and is biased by a spring member disposed within or adjacent to the surgical plate.

In one exemplary embodiment, the present invention provides a surgical plate device, including: a surgical plate structure defining one or more surgical screw receiving holes; and a surgical screw locking mechanism associated with each of the one or more surgical screw receiving holes, wherein the surgical screw locking mechanism includes a tab structure that is biased to protrude into and obstruct a portion of the corresponding screw receiving hole. The tab structure is configured to translate out of the corresponding screw receiving hole when a head of a screw is disposed within the screw receiving hole until the head of the screw passes below a plane of the tab structure. The tab structure is biased to protrude into and obstruct a portion of the corresponding screw receiving hole by a spring member coupled to the tab structure. Optionally, the tab structure is disposed at least partially within an interior portion of the surgical plate structure. Alternatively, the tab structure is disposed at least partially adjacent to a surface of the surgical plate structure. Alternatively, the tab structure is disposed at least partially between coupled layers of the surgical plate structure. Optionally, the tab structure defines a slot and selectively translates along a pin coupled to the plate structure. When a screw is fully seated in the corresponding screw receiving hole, a head of the screw is spaced apart from the corresponding tab structure. Optionally, the surgical plate device is a cervical plate device.

In another exemplary embodiment, the present invention provides a surgical plate method, including: providing a surgical plate structure defining one or more surgical screw receiving holes; and providing a surgical screw locking mechanism associated with each of the one or more surgical screw receiving holes, wherein the surgical screw locking mechanism includes a tab structure that is biased to protrude into and obstruct a portion of the corresponding screw receiving hole. The tab structure is configured to translate out of the corresponding screw receiving hole when a head of a screw is disposed within the screw receiving hole until the head of the screw passes below a plane of the tab structure. The tab structure is biased to protrude into and obstruct a portion of the corresponding screw receiving hole by a spring member coupled to the tab structure. Optionally, the tab structure is disposed at least partially within an interior portion of the surgical plate structure. Alternatively, the tab structure is disposed at least partially adjacent to a surface of the surgical plate structure. Alternatively, the tab structure is disposed at least partially between coupled layers of the surgical plate structure. Optionally, the tab structure defines a slot and selectively translates along a pin coupled to the plate structure. When a screw is fully seated in the corresponding screw receiving hole, a head of the screw is spaced apart from the corresponding tab structure. Optionally, the surgical plate device is a cervical plate device.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Again, in various exemplary embodiments, the present invention provides a surgical plate device that incorporates a screw locking mechanism in each screw hole by which the surgical plate device is affixed to a bony segment. The screw locking mechanism includes a tab structure emanating from an interior portion (or either surface) of the surgical plate that is biased into a portion of the corresponding screw hole. When a screw is inserted into the screw hole, the head of the screw temporarily biases the tab structure out of the screw hole, until the head of the screw passes below the plane of the tab structure, at which point the tab structure rebounds into the previously occupied portion of the screw hole, thereby covering a portion of the head of the screw and preventing it from "backing out." To achieve this functionality, the tab structure translates along a slot and pin or other track structure and is biased by a spring member disposed within or adjacent to the surgical plate.

Figure 1:
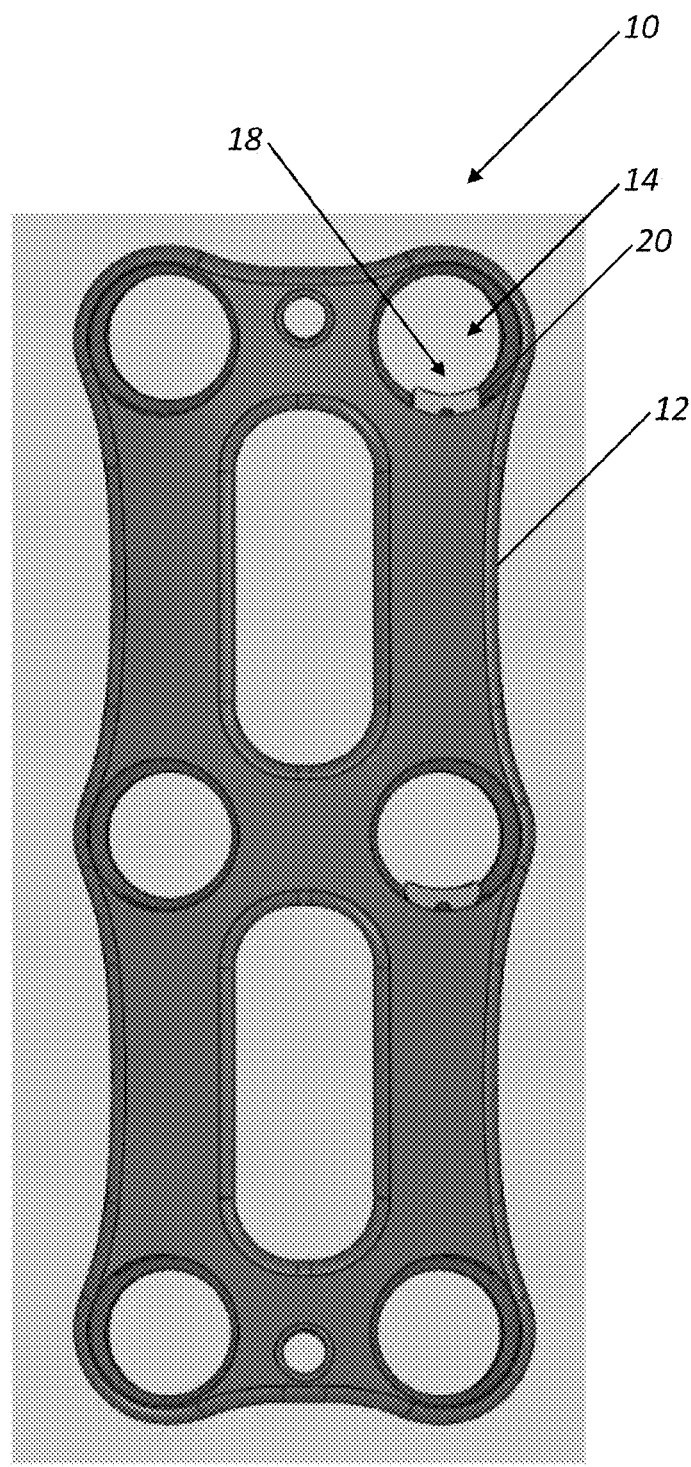
FIG. 1 is a top planar view of one exemplary embodiment of the cervical plate and cervical plate screw locking mechanism of the present invention, without cervical plate screws engaged in the cervical plate.
Figure 2:
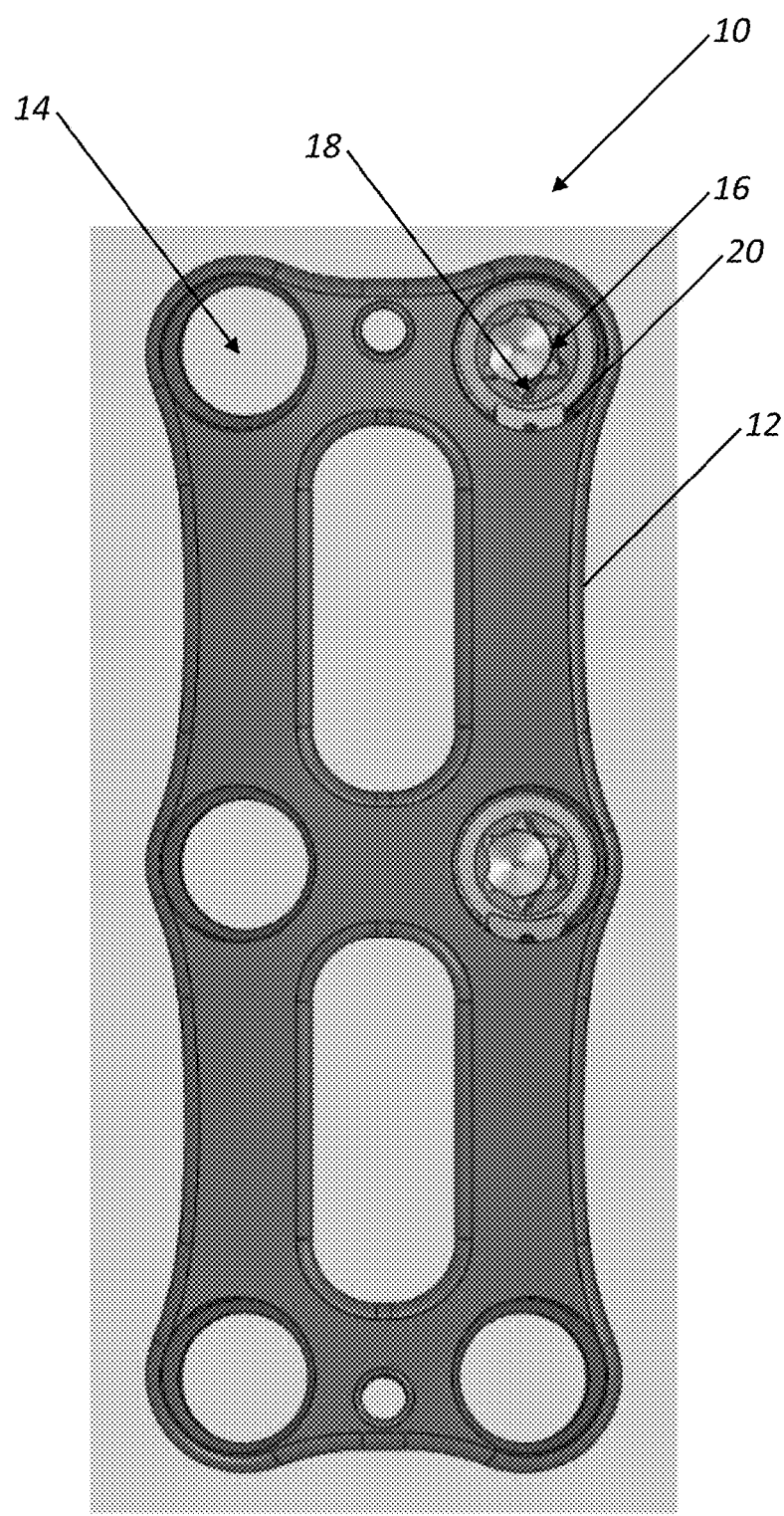
FIG. 2 is another top planar view of one exemplary embodiment of the cervical plate and cervical plate screw locking mechanism of the present invention, with cervical plate screws engaged in the cervical plate.

Referring now specifically to FIGS. 1 and 2, in one exemplary embodiment, the cervical plate device 10 of the present invention includes a plate structure 12 defining one or more recessed screw holes 14. Each of the recessed screw holes 14 is configured to receive a corresponding screw 16 (FIG. 2). The screws 16 are disposed through the recessed screw holes 14 and driven into the bony segments beneath the plate structure 12, thereby securing the plate structure 12 to the bony segments. Optionally, the screws 16 are positioned to correspond with adjacent vertebral levels of the cervical spine. The plate structure 12 is manufactured from a surgically implantable biocompatible material, such as a selected metal or composite, and has a length/width on the order of a few centimeters and a thickness on the order of a few millimeters. The screws 16 are also manufactured from a surgically implantable biocompatible material, such as a selected metal or composite, and have a length on the order of a few millimeters to a few centimeters. It will be readily apparent to those of ordinary skill in the art that the screws 16 may be manufactured to accept a hex driver or any other suitable driver, and may be replaced with other securing mechanisms that would perform similar functions. Preferably, once in place, the head 17 (FIG. 6) of each of the screws 16 sits substantially recessed beneath or flush with the surface of the plate structure 12.

The cervical plate device 10 of the present invention also includes a screw locking mechanism 18 associated with each of the recessed screw holes 14. The screw locking mechanism 18 includes a tab structure 20 that is biased to protrude into and obstruct a portion of the corresponding recessed screw hole 14. This tab structure 20 may have any suitable shape, but a tab structure 20 having a substantially arcuate end portion is illustrated. The tab structure 20 is configured to translate out of the corresponding recessed screw hole 14 when the head 17 of the screw 16 is disposed within the recessed screw hole 14 until the head 17 of the screw 16 passes below a plane 22 (FIG. 6) of the tab structure 20.

Figure 3:
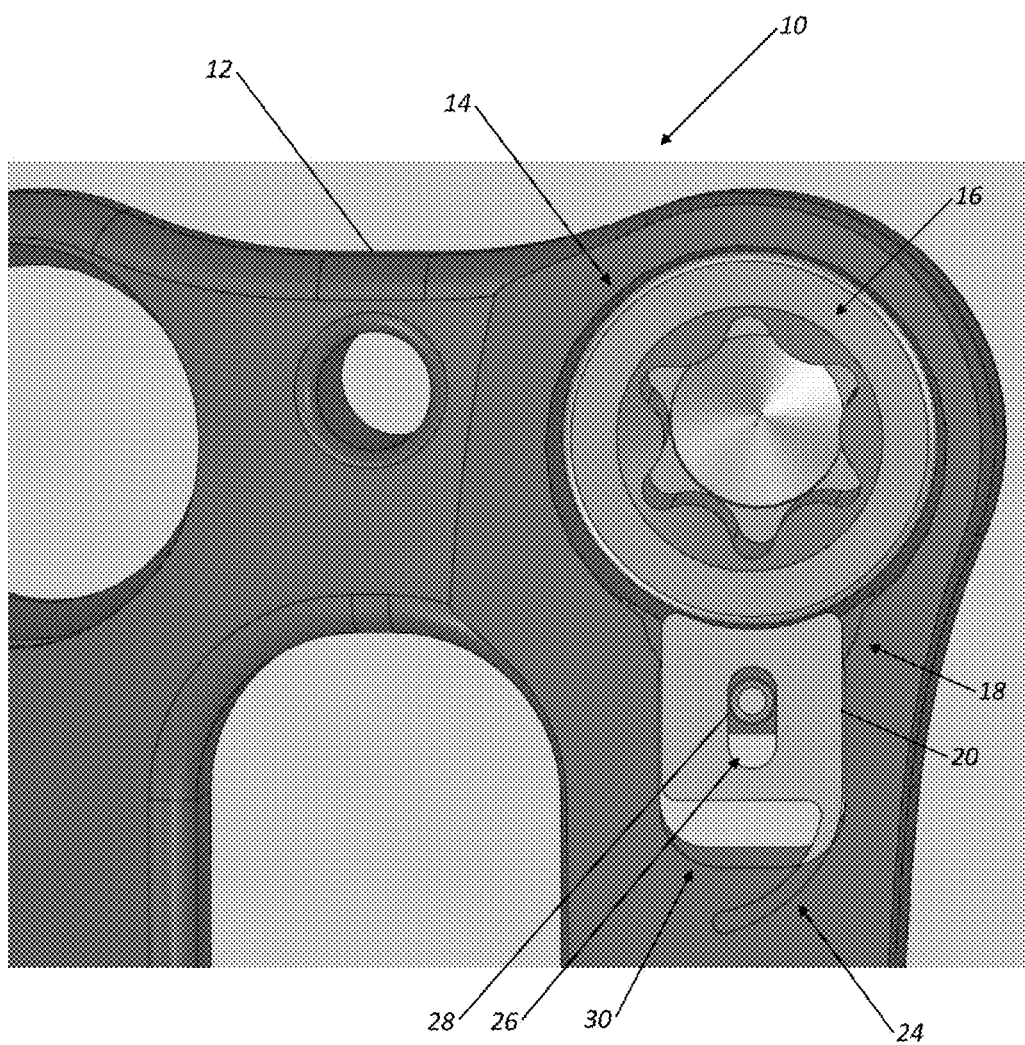
FIG. 3 is a partial top planar view of one exemplary embodiment of the cervical plate and cervical plate screw locking mechanism of the present invention, with the cervical plate screw locking mechanism in an un-deployed configuration.
Figure 4:
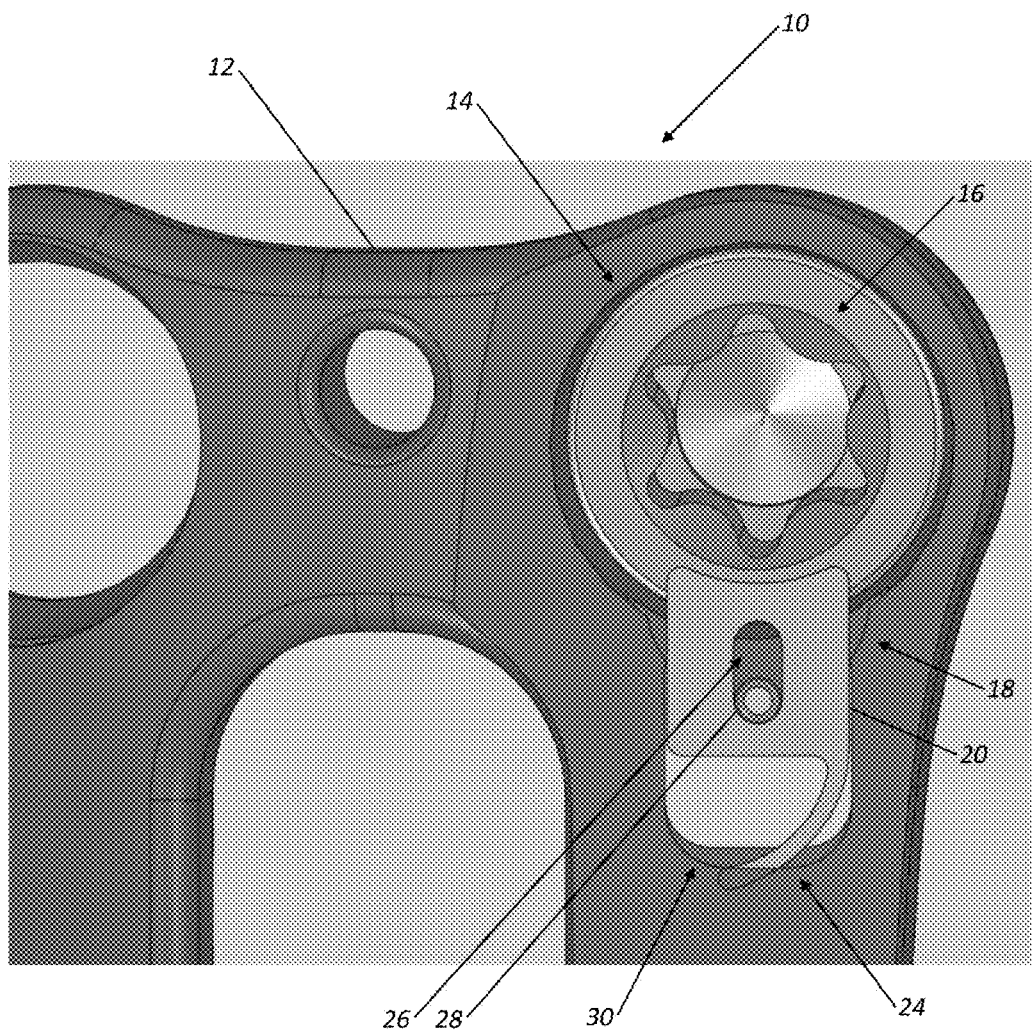
FIG. 4 is another partial top planar view of one exemplary embodiment of the cervical plate and cervical plate screw locking mechanism of the present invention, with the cervical plate screw locking mechanism in a deployed configuration.

Referring now specifically to FIGS. 3 and 4, in one exemplary embodiment, the tab structure 20 is biased to protrude into and obstruct a portion of the corresponding recessed screw hole 14 by a spring member 24 coupled to the tab structure 20. Although an arm spring is illustrated in FIGS. 3 and 4, it will be readily apparent to those of ordinary skill in the art that other types of springs or biasing members may also be used. Optionally, the tab structure 20 is disposed at least partially within an interior portion of the plate structure 12. Alternatively, the tab structure 20 is disposed at least partially adjacent to a surface of the plate structure 12. Alternatively, the tab structure 20 is disposed at least partially between coupled layers of the plate structure 12. In this exemplary embodiment, the tab structure 20 defines a slot 26 and selectively translates along a pin 28 coupled to the plate structure 12. When the screw 16 is fully seated in the corresponding recessed screw hole 14, a head 17 (FIG. 6) of the screw 16 is spaced apart from the corresponding tab structure 20.

From a manufacturing standpoint, the tab structure 20 is coupled to the plate structure 12 by inserting it into a recess 30 manufactured into either surface of the plate structure, or into a recess 30 manufactured into an interior portion of the plate structure 12 from the recessed screw hole 14. Once the tab structure 20 is in place, the pin 28 may be inserted through the slot 26 to capture the tab structure 20, and the pin 28 may then be laser welded to the plate structure 12.

Figure 5:
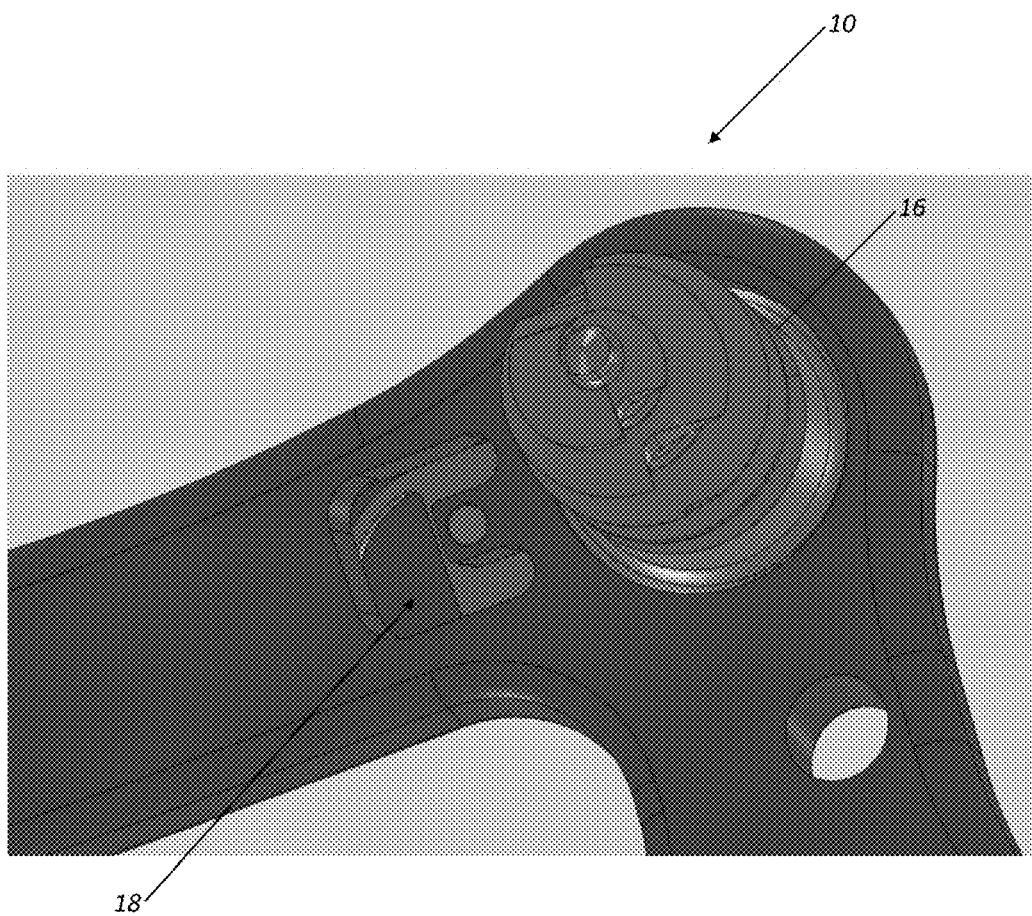
FIG. 5 is partial bottom perspective view of one exemplary embodiment of the cervical plate and cervical plate screw locking mechanism of the present invention, with a cervical plate screw engaged in the cervical plate.

FIG. 5 is partial bottom perspective view of one exemplary embodiment of the cervical plate 10 and cervical plate screw locking mechanism 18 of the present invention, with a cervical plate screw 16 engaged in the cervical plate 10.

Figure 6:
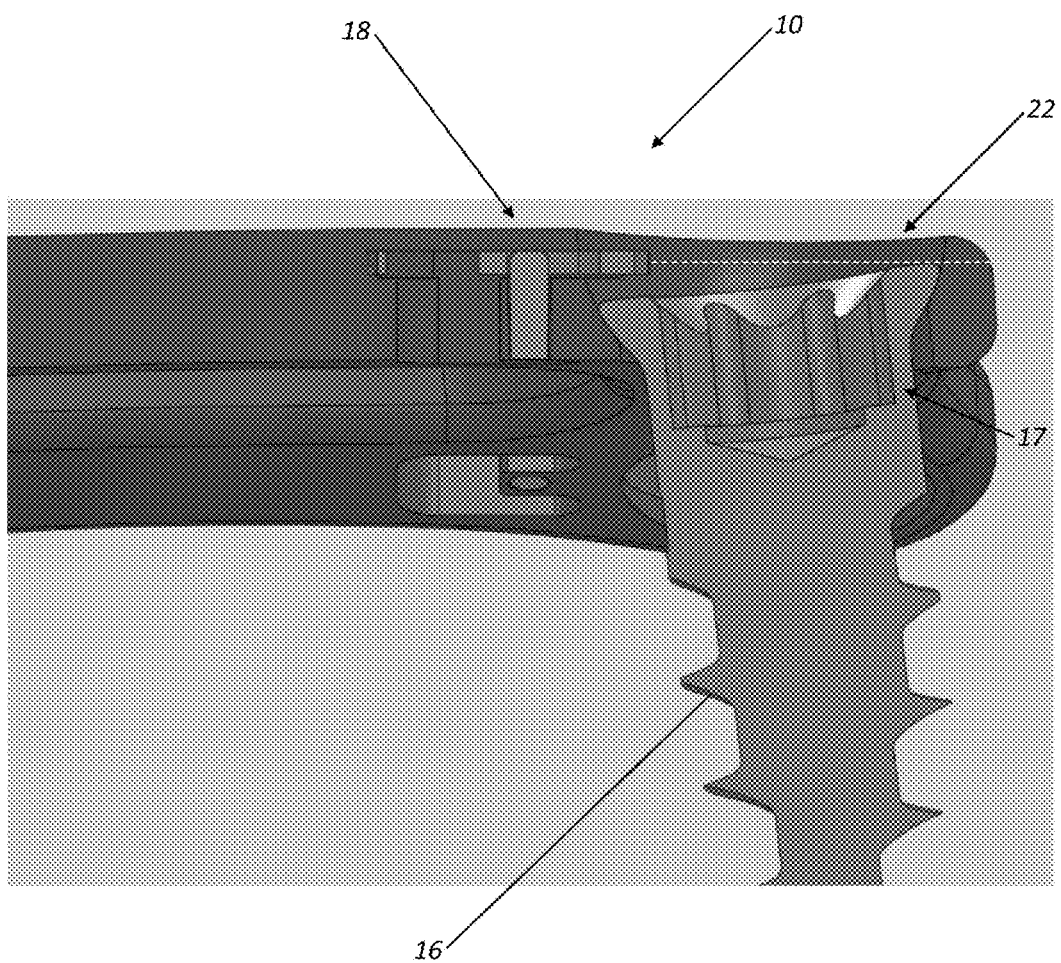
FIG. 6 is a side cross-sectional view of one exemplary embodiment of the cervical plate and cervical plate screw locking mechanism of the present invention, with a cervical plate screw engaged in the cervical plate and the cervical plate screw locking mechanism in a deployed configuration.

FIG. 6 is a side cross-sectional view of one exemplary embodiment of the cervical plate 10 and cervical plate screw locking mechanism 18 of the present invention, with a cervical plate screw 16 engaged in the cervical plate 10 and the cervical plate screw locking mechanism 18 in a deployed configuration, the head 17 of the screw 16 being below the plane 22 of and spaced apart from the corresponding tab structure 20.

Although a cervical plate, cervical plate screw locking mechanism, and cervical plate screws are primarily illustrated and described herein, it will be readily apparent to those of ordinary skill in the art that the concepts of the present invention may be extended to any similar type of surgical construct utilizing a plate and screws for bony fixation. Accordingly, any/all of the components of the cervical plate, cervical plate screw locking mechanism, and cervical plate screws may be manufactured from a surgically compatible material and are sized/shaped in a conventional manner, depending on the specific surgical application.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical plate device, comprising:
a surgical plate structure defining one or more surgical screw receiving holes; and
a surgical screw locking mechanism associated with each of the one or more surgical screw receiving holes, wherein the surgical screw locking mechanism comprises a tab structure that is biased to protrude into and obstruct a portion of the corresponding screw receiving hole;
wherein, when a screw is fully seated in the corresponding screw receiving hole, the screw is angulated at a non-perpendicular angle to the surgical plate structure and a portion of a head of the screw is spaced apart from the corresponding tab structure and an opposed portion of the head of the screw intersects a plane of translation of the corresponding tab structure;
wherein the tab structure is biased to protrude into and obstruct a portion of the corresponding screw receiving hole by a spring member coupled to the tab structure;
wherein the tab structure defines a closed slot and selectively translates into and out of the screw receiving hole along a fixed pin coupled to the plate structure and disposed through the closed slot, wherein the closed slot limits translation of the tab structure into and out of the screw receiving hole in both opposed directions with respect to the fixed pin; and
wherein one tab structure is used per screw receiving hole.

2. The surgical plate device of claim 1, wherein the tab structure is configured to translate out of the corresponding screw receiving hole when the head of the screw is disposed within the screw receiving hole until the head of the screw passes below a plane of the tab structure.

3. The surgical plate device of claim 1, wherein the tab structure is disposed at least partially within an interior portion of the surgical plate structure.

4. The surgical plate device of claim 1, wherein the tab structure is disposed at least partially adjacent to a surface of the surgical plate structure.

5. The surgical plate device of claim 1, wherein the tab structure is disposed at least partially between coupled layers of the surgical plate structure.

6. The surgical plate device of claim 1, wherein the surgical plate device comprises a cervical plate device.

7. A surgical plate method, comprising:
providing a surgical plate structure defining one or more surgical screw receiving holes; and
disposing a surgical screw locking mechanism adjacent to each of the one or more surgical screw receiving holes, wherein the surgical screw locking mechanism comprises a tab structure that is biased to protrude into and obstruct a portion of the corresponding screw receiving hole;
wherein, when a screw is fully seated in the corresponding screw receiving hole, the screw is angulated at a non-perpendicular angle to the surgical plate structure and a portion of a head of the screw is spaced apart from the corresponding tab structure and an opposed portion of the head of the screw intersects a plane of translation of the corresponding tab structure;
wherein the tab structure is biased to protrude into and obstruct a portion of the corresponding screw receiving hole by a spring member coupled to the tab structure;
wherein the tab structure defines a closed slot and selectively translates into and out of the screw receiving hole along a fixed pin coupled to the plate structure and disposed through the closed slot, wherein the closed slot limits translation of the tab structure into and out of the screw receiving hole in both opposed directions with respect to the fixed pin; and
wherein one tab structure is used per screw receiving hole.

8. The surgical plate method of claim 7, wherein the tab structure is configured to translate out of the corresponding screw receiving hole when the head of the screw is disposed within the screw receiving hole until the head of the screw passes below a plane of the tab structure.

9. The surgical plate method of claim 7, wherein the tab structure is disposed at least partially within an interior portion of the surgical plate structure.

10. The surgical plate method of claim 7, wherein the tab structure is disposed at least partially adjacent to a surface of the surgical plate structure.

11. The surgical plate method of claim 7, wherein the tab structure is disposed at least partially between coupled layers of the surgical plate structure.

12. The surgical plate method of claim 7, wherein the surgical plate device comprises a cervical plate device.

* * * * *